(12) United States Patent
Ellenz

(10) Patent No.: US 6,923,571 B2
(45) Date of Patent: Aug. 2, 2005

(54) TEMPERATURE-BASED SENSING DEVICE FOR DETECTING PRESENCE OF BODY PART

(75) Inventor: John David Ellenz, Olathe, KS (US)

(73) Assignee: Compliance Laboratories, L.L.C., Lenexa, KS (US)

(*) Notice: Subject to any disclaimer, the term of this patent is extended or adjusted under 35 U.S.C. 154(b) by 19 days.

(21) Appl. No.: 10/360,439

(22) Filed: Feb. 5, 2003

(65) Prior Publication Data

US 2003/0152133 A1 Aug. 14, 2003

Related U.S. Application Data

(60) Provisional application No. 60/355,116, filed on Feb. 8, 2002.

(51) Int. Cl.[7] ............................. G01N 25/00; G01K 3/00
(52) U.S. Cl. ........................... 374/45; 374/141; 374/107
(58) Field of Search .......................... 374/141, 45, 163, 374/107, 166; 340/573.1, 586, 573.4, 589, 588, 539.27

(56) References Cited

U.S. PATENT DOCUMENTS

| | | | |
|---|---|---|---|
| 4,747,413 A | * | 5/1988 | Bloch ........................... 600/549 |
| 5,543,780 A | * | 8/1996 | McAuley et al. ........... 340/572.1 |
| 5,635,909 A | * | 6/1997 | Cole ............................. 340/586 |
| 5,802,611 A | * | 9/1998 | McKenzie et al. ................ 2/69 |
| 5,973,602 A | * | 10/1999 | Cole et al. ................... 340/584 |
| 5,982,285 A | * | 11/1999 | Bueche et al. ............ 340/573.1 |
| 6,102,856 A | * | 8/2000 | Groff et al. .................. 600/301 |
| 6,344,795 B1 | * | 2/2002 | Gehlot ......................... 340/540 |
| 6,349,201 B1 | * | 2/2002 | Ford ......................... 455/404.1 |
| 6,381,482 B1 | * | 4/2002 | Jayaraman et al. .......... 600/388 |
| 2003/0076867 A1 | * | 4/2003 | Mundt et al. ................... 374/45 |
| 2003/0078528 A1 | * | 4/2003 | Rahman et al. ................. 602/5 |
| 2003/0154990 A1 | * | 8/2003 | Parker ......................... 128/861 |
| 2003/0214408 A1 | * | 11/2003 | Grajales et al. ........... 340/573.1 |

FOREIGN PATENT DOCUMENTS

| | | | | |
|---|---|---|---|---|
| JP | 01170888 A | * | 7/1989 | ............ G01V/9/04 |
| JP | 01173893 A | * | 7/1989 | ............ G01V/9/04 |
| JP | 02311783 A | * | 12/1990 | ............ G01V/9/04 |

* cited by examiner

Primary Examiner—Christopher W. Fulton
Assistant Examiner—Mirellys Jagan
(74) Attorney, Agent, or Firm—Hovey Williams LLP

(57) ABSTRACT

A temperature-based sensing device (10) for detecting or determining a presence or proximity of a body or body part (12) in or near a garment, device, apparatus, or other item (14), such as, for example, an orthopedic device or exercise apparatus. The device (10) broadly comprises a first temperature sensor (20) for measuring a first or internal temperature of a an interior or receiving portion (16) of the item (14); a second temperature sensor (22) for measuring a second or external temperature of an ambient environment (18) surrounding the item (14); a controller (24) adapted to determine the presence of the body part (12) by comparing the first temperature with the second temperature; and connective circuitry (26) made of flexible material and adapted to electrically connect at least the first temperature sensor (20) with the controller (24).

17 Claims, 2 Drawing Sheets

TEMPERATURE-BASED SENSING DEVICE FOR DETECTING PRESENCE OF BODY PART

RELATED APPLICATIONS

The present application is related to and claims priority benefit of a co-pending provisional patent application titled "Temperature Sensor for Detecting Presence of a Human Body in a Garment or Apparatus", Ser. No. 60/355,116, filed Feb. 8, 2002, the content of which is hereby incorporated into the present application by reference.

BACKGROUND OF THE INVENTION

1. Field of the Invention

The present invention relates broadly to sensors or sensing devices for detecting or determining a presence or proximity of a body part. More particularly, the present invention concerns a sensing device for detecting or determining a presence or proximity of a body or body part in or near a garment, device, apparatus, or other item, such as, for example, an orthopedic device or exercise apparatus, wherein the presence of the body part is detected as a change or difference between a first temperature of a receiving or interior portion of the item and a second temperature of an ambient environment surrounding the item.

2. Description of the Prior Art

It is often desirable to detect or determine whether a human body or body part is present or nearby. This is particularly true, for example, when it is desired or required to determine whether a patient or other person is wearing an orthopedic device or using an exercise apparatus with a frequency and duration as directed. To that end, prior art devices exist that use a variety of techniques for accomplishing such detection. Prior art devices are known, for example, that are based on direct electrically conductive contact with the body part. Other prior art devices are known that are based on pressure exerted by the body part.

Unfortunately, these prior art devices suffer from a number of problems and disadvantages. Detection based on direct electrically conductive contact with the body part, for example, does not work or does not work as effectively when clothing, padding, or other fabric or material is interposed between the prior art device and the body part. Similarly, detection based on exerted pressure is not suitable for all situations, such as, for example, when the exerted pressure is unpredictable or insufficient. Furthermore, even where exerted pressure is predictably present and sufficient in force and duration, the positioning of the prior art device becomes crucial and may undesirably dictate the positioning or design of other components or the item generally.

Due to the above-identified and other problems and disadvantages in the art, a need exists for an improved sensing mechanism for detecting a presence of a body part.

SUMMARY OF THE INVENTION

The present invention overcomes the above-described and other problems and disadvantages in the prior art with a temperature-based sensing device adapted to detect or determine a presence or proximity of a body or body part in a garment, orthopedic device, exercise apparatus, or other item.

In a preferred embodiment, the device broadly comprises a first or internal temperature sensor; a second or external temperature sensor; a controller; and connective circuitry. The first temperature sensor is operable to sense a first temperature of a receiving or interior portion of the item, and to generate a first electrical signal corresponding to the first temperature. The second temperature sensor is operable to sense a second temperature of an ambient environment surrounding the item, and to generate a second electrical signal corresponding to the second temperature.

The controller is operable to receive and compare the first electrical signal and the second electrical to identify a degree and rate of increase, if any, of the first temperature relative to the second temperature. If the first temperature rises at a certain minimum rate relative to the second temperature, and reaches a certain minimum temperature range, and exceeds a certain temperature threshold relative to the second temperature, then the controller determines that the body part is present.

The connective circuitry is operable to electrically connect the first temperature sensor and, as appropriate, the second temperature sensor with the controller. One or more of the first temperature sensor, second temperature sensor, controller, and connective circuitry is preferably comprised of substantially flexible material so that, when embedded or incorporated into the item, the user's or wearer's comfort is not unduly affected.

Thus, it will be appreciated that the device of the present invention provides a number of substantial advantages over the prior art, including, for example, using temperature, rather than direct electrically conductive contact or exerted pressure, to determine the presence of the body part, and thereby accommodating a greater variety of applications. Furthermore, the physical flexibility of the first temperature sensor, second temperature sensor, controller, or connective circuitry, as appropriate, advantageously allows for incorporating these components of the device directly into the item without substantially affecting the wearer's or user's comfort.

These and other important features of the present invention are more fully described in the section titled DETAILED DESCRIPTION OF A PREFERRED EMBODIMENT, below.

BRIEF DESCRIPTION OF THE DRAWINGS

A preferred embodiment of the present invention is described in detail below with reference to the attached drawing figures, wherein.

DETAILED DESCRIPTION OF A PREFERRED EMBODIMENT

Figure 1:
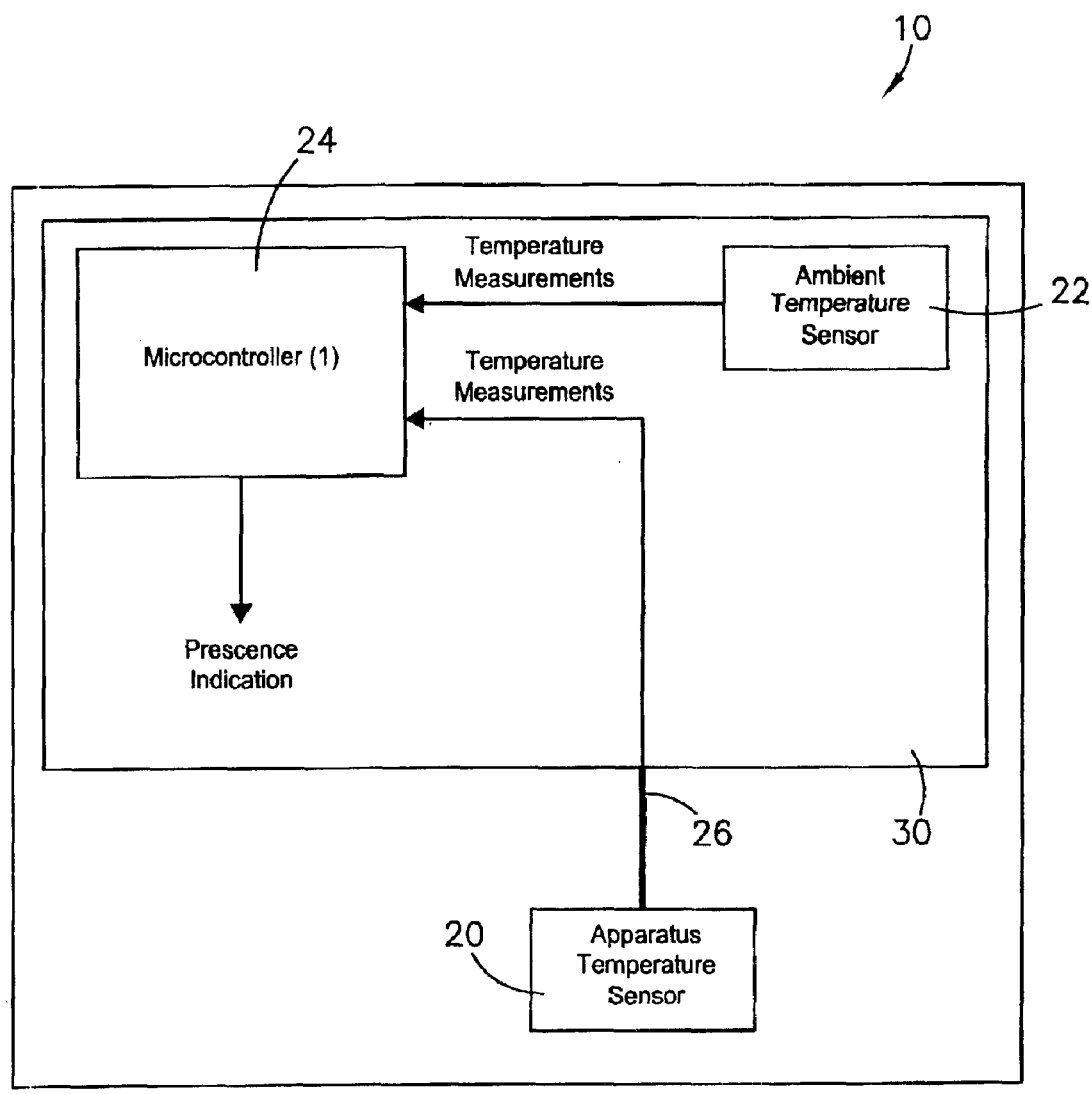
FIG. 1 is a block diagram of a preferred embodiment of a temperature-based sensing device of the present invention.
Figure 2:
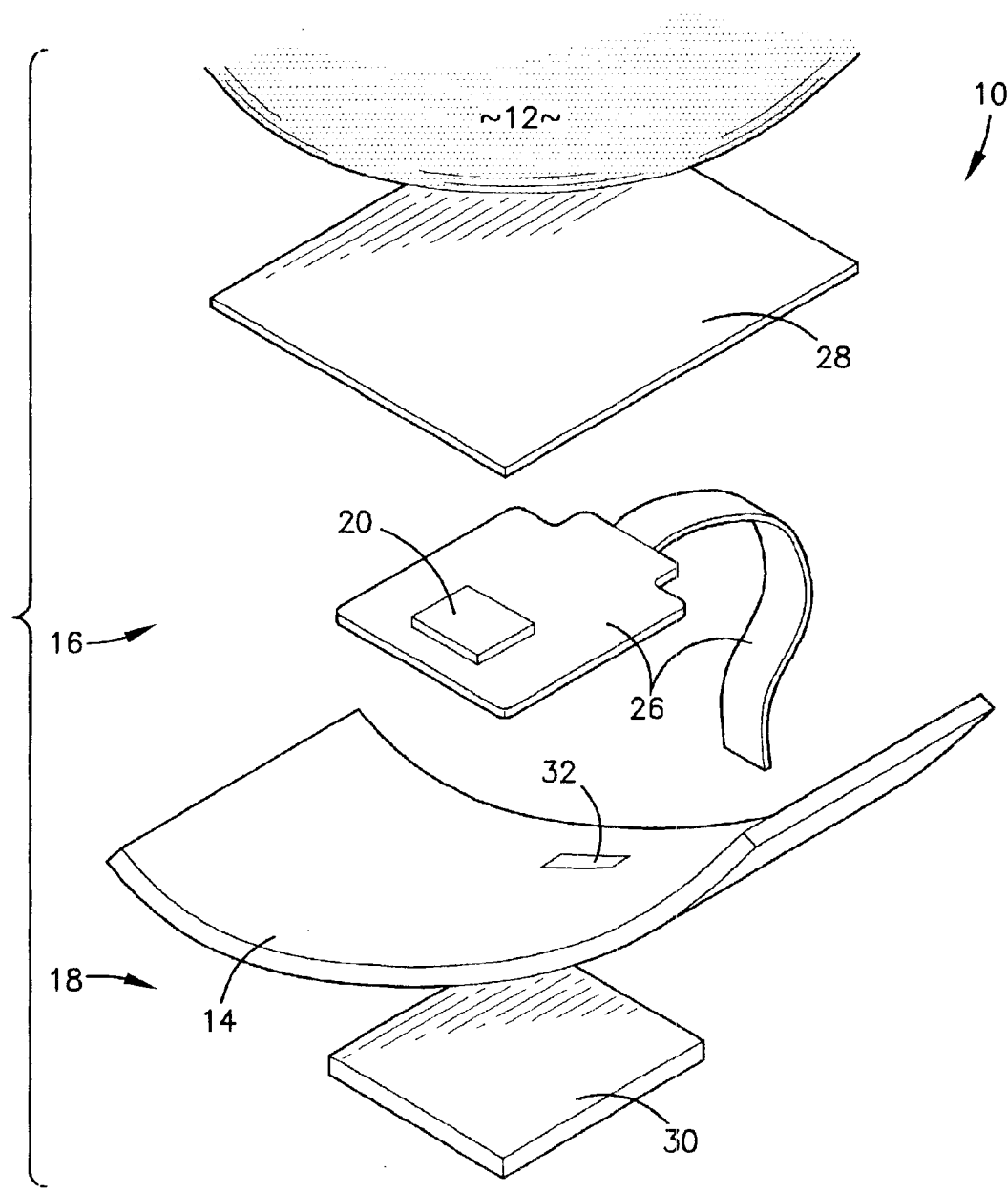
FIG. 2 is a sectional view of the sensing device of FIG. 1 during exemplary operation.

Referring to the figures, a temperature-based sensing device 10 is shown constructed in accordance with a preferred embodiment of the present invention. The device 10 is adapted to detect or determine a presence or proximity of a body or body part 12 relative to an item 14 based upon a change or difference between a first temperature of a receiving or interior portion 16 of the item 14 and a second temperature of an ambient environment 18 surrounding the item 14. By way of example and not limitation, it will be appreciated that a potential application for the device 10 is to monitor use of a garment, orthopedic device, or exercise apparatus.

In the preferred embodiment, the device 10 broadly comprises a first or internal temperature sensor 20; a second or external temperature sensor 22; a controller 24; and connective circuitry 26. The first or internal temperature sensor 20 is operable to sense a first or internal temperature of the receiving or interior portion 16 of the item 14 where the body part 12 would be located if it were present, and to generate a first electrical signal corresponding thereto. The first temperature sensor 20 may be any substantially conventional temperature sensing element, preferably comprised of a flexible material, embedded or otherwise incorporated into the item 14 so as to be substantially exposed, but for any intervening material 28, to the body part 12 when the body part 12 is present. The second or external temperature sensor 22 is operable to sense a second or external temperature of the ambient environment 18 surrounding the item 14, and to generate a second electrical signal corresponding thereto. The second temperature sensor 22 may be any substantially conventional temperature sensing element, preferably comprised of a flexible material, embedded or otherwise incorporated into the item 14 so as to be substantially exposed, but for any intervening material, to the ambient environment 18 surrounding the item 14.

The controller 24 is operable to receive and process the first and second electrical signals from, respectively, the first and second temperature sensors 20,22 in order to determine the presence of the body part 12. In more detail, the controller 24 compares the first electrical signal to the second electrical to identify a degree and rate of increase, if any, of the first temperature relative to the second temperature. If the first temperature rises at a certain minimum rate relative to the second temperature, and reaches a certain minimum temperature range, and exceeds a certain temperature threshold relative to the second temperature, then the controller 24 determines that the body part 12 is present in the receiving or interior portion 16 of the item 14. The minimum rate, minimum temperature range, and temperature threshold are all predetermined to reliably establish whether an increase in the first temperature relative to the second temperature is due to the presence of the body part 12 and the body heat associated with it. It will be appreciated by those with ordinary skill in the art that these values will vary substantially depending on the materials used in constructing both the device 10 and the item 12; on the placement of the various components of the device 10, particularly the first and second temperature sensors 20,22; and on other application dependent factors and considerations. The controller 24 may be implemented in software, firmware, or hardware, or any combination thereof, and may use any substantially conventional control device, such as, for example, a microcontroller or microprocessor.

In a preferred implementation, both the controller 24 and the second temperature sensor 22 are included and housed in a hardware block 30. Given that the second temperature sensor 22 must be substantially exposed to the ambient environment 18, and given that it is often desirable to locate the controller 24 so as to facilitate easy and convenient access from the ambient environment 18, housing these two components together in the hardware block 30 will typically be particularly practical and desirable.

The connective circuitry 26 is operable to electrically connect the first temperature sensor 20 with the controller 24. The same or similar connective circuitry may be used to electrically connect the second temperature sensor 22 with the controller 24 where appropriate (e.g., they are not both housed in the hardware block 30). The connective circuitry 26 may be comprised of connectors, wiring harnesses, flexible circuitry, or any combination thereof.

Some or all of the first temperature sensor 20, second temperature sensor 22, controller 24, and connective circuitry 26 is preferably comprised of one or more substantially flexible materials so that, when embedded or otherwise incorporated into the item 14, the user's or wearer's comfort is not unduly affected.

In exemplary use and operation, the device 10 is attached, embedded, or otherwise incorporated into the garment, orthopedic device, exercise apparatus, or other item 14. The first temperature sensor 20 is incorporated into the item 14 so as to be substantially exposed to the body part 12 when the body part 12 is present. As desired, a plurality of first temperature sensors 20 may be used so as to more reliably detect the presence of the body part 12. The one or more first temperature sensors 20 are each electrically connected to the controller 24 by the connective circuitry 26. As mentioned, the connective circuitry 26 is preferably comprised of substantially flexible material so that the user's or wearer's comfort is not unduly affected. Cloth, foam, padding, plastic, or other material 28 may cover and protect the first temperature sensor 20 or be otherwise interposed between the first temperature sensor 20 and the body part 12.

The second temperature sensor 22 and the controller 24 are included in the hardware block 30, which is incorporated into the item 14 so that the second temperature sensor 22 is substantially exposed to the ambient environment 18 surrounding the item 14. As required or desired, one or more slots 32 or paths may be manufactured or cut into the item 14 to allow for routing the connective circuitry 26.

Continuously or periodically, the first temperature sensor 20 generates and sends to the controller 24 the first electrical signal corresponding to the first temperature of the receiving or interior portion 16 of the item 14. Similarly, continuously or periodically, the second temperature sensor 22 generates and sends to the controller 24 the second electrical signal corresponding to the second temperature of the ambient environment 18. As mentioned, the controller 24 receives and compares the first electrical signal and the second electrical signal to identify a degree and rate of increase, if any, of the first temperature relative to the second temperature. If the first temperature rises at a certain minimum rate relative to the second temperature, and reaches a certain minimum temperature range, and exceeds a certain temperature threshold relative to the second temperature. As mentioned, the minimum rate, minimum temperature range, and temperature threshold are all predetermined to reliably establish, for the particular application, whether an increase in the first temperature relative to the second temperature is due to the presence of the body part 12 and the body heat associated with it. If the controller 24 determines that the body part 12 is present, then some appropriate action takes place (e.g., writing the date and time to a local or remote memory).

From the preceding description, it will be appreciated that the device 10 of the present invention provides a number of substantial advantages over the prior art, including, for example, using temperature, rather than direct electrically conductive contact or exerted pressure, to determine the presence of the body part 12, thereby accommodating a greater variety of applications. Furthermore, the physical flexibility of the first and second temperature sensors 20,22, controller 24, and connective circuitry 26, as appropriate, advantageously allows for incorporating these components of the device 10 directly into the item 14 without substantially affecting the wearer's or user's comfort.

Although the invention has been described with reference to the preferred embodiments illustrated in the attached drawings, it is noted that equivalents may be employed and substitutions made herein without departing from the scope of the invention as recited in the claims. It will be appreciated, for example, that, as mentioned, the controller may be implemented in software, firmware, or hardware, or any combination thereof, and may use any substantially conventional control device, such as, for example, a microcontroller or microprocessor.

Having thus described the preferred embodiment of the invention, what is claimed as new and desired to be protected by Letters Patent includes the following:

1. A device for detecting a presence of a body part relative to an item, the device comprising:
    a first temperature sensor operable to generate a first electrical signal corresponding to a first temperature of a receiving portion of the item;
    a second temperature sensor operable to generate a second electrical signal corresponding to a second temperature of an ambient environment surrounding the item; and
    a controller that determines the presence of the body part based at least in part upon a comparison of the first electrical signal and the second electrical signal, wherein the comparison includes analyzing a rate of change of at least one of the temperatures.

2. The device as set forth in claim 1, wherein the item is a garment.

3. The device as set forth in claim 1, wherein the first temperature sensor is incorporated into the item.

4. The device as set forth in claim 1, wherein the controller is further operable to determine the presence of the body part based upon a rate of change of the first electrical signal relative to the second electrical signal.

5. The device as set forth in claim 1, wherein the controller is further operable to determine the presence of the body part based upon a difference between the first electrical signal and the second electrical signal.

6. The device as set forth in claim 1, wherein the controller is further operable to determine the presence of the body part based upon all three of a rate of change of the first electrical signal relative to the second electrical signal, a difference between the first electrical signal and the second electrical signal, and the first electrical signal corresponding to the first temperature being within a predetermined temperature range.

7. The device as set forth in claim 1, further including a connective circuitry extending between and electrically connecting the first temperature sensor and the controller, wherein the connective circuitry and the first temperature sensor are each comprised of one or more substantially flexible materials.

8. The device as set forth in claim 1, wherein the item is an orthopedic device.

9. The device as set forth in claim 1, wherein the item is an exercise apparatus.

10. A sensing device for detecting a presence of a body part relative to an item, the sensing device comprising:
    a first temperature sensor incorporated into the item and operable to generate a first electrical signal corresponding to a first temperature of a receiving portion of the item;
    a second temperature sensor operable to generate a second electrical signal corresponding to a second temperature of an ambient environment surrounding the item; and
    a controller that determines the presence of the body part based upon both of a rate of change of the first electrical signal relative to the second electrical signal and a degree of difference between the first electrical signal and the second electrical signal.

11. The sensing device as set forth in claim 10, wherein the item is a garment.

12. The sensing device as set forth in claim 10, wherein the item is an orthopedic device.

13. The sensing device as set forth in claim 10, wherein the item is an exercise apparatus.

14. The sensing device as set forth in claim 10, wherein the controller is further operable to determine the presence of the body part based upon all three of the rate of change of the first electrical signal relative to the second electrical signal, the degree of difference between the first electrical signal and the second electrical signal, and the first electrical signal corresponding to the first temperature being within a predetermined temperature range.

15. The sensing device as set forth in claim 10, further including a connective circuitry extending between and electrically connecting the first temperature sensor and the controller, wherein the connective circuitry and the first temperature sensor are each comprised of one or more substantially flexible materials.

16. A sensing device for detecting a presence of a body part relative to an item, the sensing device being selected from the group comprising: garments, orthopedic devices, and exercise apparatuses, the sensing device comprising:
    a first temperature sensor incorporated into the item and operable to generate a first electrical signal corresponding to a first temperature of a receiving portion of the item;
    a second temperature sensor operable to generate a second electrical signal corresponding to a second temperature of an ambient environment surrounding the item;
    a connective circuitry extending between and electrically connecting the first temperature sensor and the controller, wherein the connective circuitry and the first temperature sensor are each comprised of one or more substantially flexible materials; and
    a controller that determines the presence of the body part based upon all three of the rate of change of the first electrical signal relative to the second electrical signal, the degree of difference between the first electrical signal and the second electrical signal, and the first electrical signal corresponding to the first temperature being within a predetermined temperature range.

17. A sensing device for detecting a presence of a body part relative to an item, the sensing device being selected from the group comprising: garments, orthopedic devices, and exercise apparatuses, the sensing device comprising:
    a first temperature sensor incorporated into the item and operable to generate a first electrical signal corresponding to a first temperature of a receiving portion of the item;
    a second temperature sensor operable to generate a second electrical signal corresponding to a second temperature of an ambient environment surrounding the item;
    a connective circuitry extending between and electrically connecting the first temperature sensor and the controller, wherein the connective circuitry and the first temperature sensor are each comprised of one or more substantially flexible materials; and
    a controller that determines that the body part is present when the first temperature rises at a predetermined minimum rate relative to the second temperature, the first temperature reaches a predetermined minimum temperature range, and the first temperature exceeds a predetermined temperature threshold relative to the second temperature, wherein the controller is further configured to write a current date and time to a memory.

* * * * *